United States Patent [19]
Young

[11] Patent Number: 5,841,545
[45] Date of Patent: *Nov. 24, 1998

[54] MULTI-FUNCTION DIAMOND FILM FIBEROPTIC PROBE AND MEASURING SYSTEM EMPLOYING SAME

[75] Inventor: Jack P. Young, Oak Ridge, Tenn.

[73] Assignee: Lockheed Martin Energy Systems, Inc., Oak Ridge, Tenn.

[*] Notice: The term of this patent shall not extend beyond the expiration date of Pat. No. 5,822,072.

[21] Appl. No.: 529,128

[22] Filed: Sep. 15, 1995

Related U.S. Application Data

[63] Continuation-in-part of Ser. No. 316,306, Sep. 30, 1994, abandoned, and Ser. No. 308,855, Sep. 19, 1994, abandoned.

[51] Int. Cl.$^6$ .................................................. G01N 21/00
[52] U.S. Cl. ..................... 356/436; 385/12; 250/227.23
[58] Field of Search ............................ 356/73, 336, 133, 356/128, 432, 436, 440, 301, 317, 318, 416, 446, 326; 250/458.1, 459.1, 461.1, 461.2, 227.11, 227.23, 227.24, 227.28; 385/12, 31, 38, 85, 88, 115, 116, 133

[56] References Cited

U.S. PATENT DOCUMENTS

| | | |
|---|---|---|
| 2,071,531 | 6/1937 | Hulme . |
| 2,102,955 | 9/1937 | Hulme . |
| 4,573,761 | 3/1986 | McLachlan et al. ................. 350/96.24 |
| 4,796,671 | 1/1989 | Furushima et al. . |
| 5,013,150 | 5/1991 | Watts et al. . |
| 5,112,127 | 5/1992 | Carrabba et al. ........................ 356/301 |
| 5,155,549 | 10/1992 | Dhadwal ................................. 356/336 |
| 5,164,999 | 11/1992 | Shifflett . |
| 5,180,228 | 1/1993 | Tarumi et al. . |
| 5,201,022 | 4/1993 | Shifflett . |
| 5,332,449 | 7/1994 | Verstreken et al. . |
| 5,402,508 | 3/1995 | O'Rourke et al. ........................ 385/31 |

OTHER PUBLICATIONS

Sheng Dai et al, "Temperature Measurement by Observation of the Raman Spectrum of Diamond," *Appl. Spectros.*, 46 (1992).

Sheng Dai et al, "Measurement of Molten Salt Raman Spectra by the Use of Fiber Optics," *Mikrochim. Acta*, 108 (1992), pp. 261–264.

A. Kumar et al, "Novel Refractometer Using a Tapered Optical Fibre," *Electronics Letters*, 20 (1984) pp. 534–535.

F. B. Shand, Chapter 9, *Glass Engineering Handbook*, 2nd Ed., 1958, pp. 176–184.

Ovadia Lev et al, "A High–Sensitivity Photometric Method Based on Doped Sol–Gel Glass Detectors: Determination of Sub–ppb Divalent Iron," *Fresenius J. Anal. Chem*, (1992), pp. 370–372.

Chongmok Lee et al, "Scanning Electrochemical Microscopy: Preparation of Submicrometer Electrodes," *Anal. Chem.*, 63 (1991), pp. 78–83.

*Primary Examiner*—K. Hantis
*Attorney, Agent, or Firm*—Shelley L. Stafford

[57] ABSTRACT

A fused fiberoptic probe having a protective cover, a fiberoptic probe system, and embodiments thereof for conducting electromagnetic spectral measurements are disclosed. The fused fiberoptic probe comprises a probe tip having a specific geometrical configuration, an exciting optical fiber and at least one collection optical fiber fused within a housing, preferably silica, with a protective cover disposed over at least a portion of the probe tip. The specific geometrical configurations in which the probe tip can be shaped include a slanted probe tip with an angle greater than 0°, an inverted cone-shaped probe tip, and a lens head.

20 Claims, 7 Drawing Sheets

MULTI-FUNCTION DIAMOND FILM FIBEROPTIC PROBE AND MEASURING SYSTEM EMPLOYING SAME

RELATED APPLICATIONS AND PATENTS

The present application is a Continuation-In-Part of both co-pending U.S. patent application Ser. No. 08/316,306, filed Sep. 30, 1994 now abandoned and U.S. patent application Ser. No. 08/308,855, filed Sep. 19, 1994, now abandoned which are both incorporated herein by reference. Also, U.S. patent application Ser. No. 08/792,510 filed Jan. 31, 1997, pending, is a continuation of 08/316,306.

This invention was made with Government support under contract DE-AC05-840R21400 awarded by the Office of Industrial Processes, U.S. Department of Energy to Martin Marietta Energy Systems, Inc., and the Government has certain rights in this invention.

FIELD OF THE INVENTION

The present invention relates to instrumentation for measuring electromagnetic emissions including light scattering and luminescence, and particularly to a fused fiberoptic probe having a protective cover means exhibiting improved performance for conducting electromagnetic spectral measurements, and more particularly for conducting long-term Raman spectral measurements while the protective cover serves as a temperature sensor by measuring the ratio of the Stokes to anti-Stokes Raman scattering of the protective cover in high temperature, corrosive environments remote from the optical energy-generating source and signal analyzer.

BACKGROUND OF THE INVENTION

Measuring certain physical and chemical characteristics using light has been known in laboratories for many years. Spectroscopic techniques are frequently used in laboratories for both qualitative and quantitative analyses. The combination of lasers and optical fibers have greatly increased activity in this field. The use of optical fibers, in particular, have allowed the locating of sensitive and expensive equipment remote from harsh reactor environments, thus making spectroscopic analysis techniques suitable for application to commercial processes.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure. For process control or for analyses of samples in remote or hostile environments, it is often desirable to measure the vibrational spectrum of a sample in that process stream or environment. If the vibrational spectrum is to be measured by an optical absorption process, optical fibers must be used so that optical energy from a source is delivered to a sample via one fiber, and after passage through the sample, an optical signal generated by the exciting optical energy is collected by the same or, more preferably, another fiber. This collected light is directed to a monochrometer/or a photodetector for analyzing its wavelength and/or intensity.

One analytical technique that is useful for commercial applications is Raman spectroscopy. When exciting optical energy of a single wavelength interacts with a molecule, the optical energy scattered by the molecule contains small amounts of optical energy having wavelengths different from that of the incident exciting optical energy. This is known as the Raman effect. The wavelengths present in the scattered optical energy are characteristic of the structure of the molecule, and the intensity of this optical energy is dependent on the concentration of these molecules. Thus, the identities and concentrations of various molecules in a substance can be determined by illuminating the substance with energy of a single wavelength and then measuring the individual wavelengths, and their intensities, in the scattered optical energy.

Raman spectroscopy provides a means for obtaining similar molecular vibrational spectra over optical fibers using visible or near infrared light that is transmitted by the optical fibers without significant absorption losses. In Raman spectroscopy, monochromatic light is directed to a sample and the spectrum of the light scattered from the sample is determined. In a typical Raman experiment, the excitation light source is a laser line, such as the 514.5 nm (19435 cm$^{-1}$) line from an Argon ion gas laser. The Raman effect is not usually a sensitive effect; most of the light scattered from the sample will also be of the exciting wavelength (the Rayleigh line). Approximately 1 part in $10^6$ will be scattered at wavelengths containing the sum or difference of the Rayleigh and allowed molecular vibrational frequencies. For example, if a molecule has a Raman active vibration at 5 $\mu$m (2000 cm$^{-1}$), the line will appear in the scattered light spectrum at 19435+2000 cm$^{-1}$ or 466 nm. Since this scattered signal is very weak, an intense exciting source, such as a laser, is preferable and the optical arrangement for receiving these signals should be optimized.

Measurements of laser Raman spectroscopy using optical fibers have recently become an active area of study. The technique requires minimum alignment of samples with respect to an input laser beam or collection optics, and the sample may be located some distance from the spectrometer in a hostile environment. So far, most of the probes employed in these measurements have been constructed by sealing the collection optical fibers and one laser input fiber into a metal or glass protective tube with an epoxy cement. This imposes difficulties for the measurement of Raman spectra with these probes in some hostile environments due to chemical and/or thermal reactions of the epoxy resin with surrounding molecules. The measurement of molten salt Raman spectra is an example in which the extremely corrosive conditions and high temperatures involved are enough to degrade the epoxy materials.

Obtaining Raman spectra through optical fibers over long distances is historically difficult. Sending intense laser light through long lengths of optical fiber gives rise to false optical signals that originate both from fluorescence and Raman scattering arising from the fiber core and cladding. Similarly, the scattered Rayleigh radiation can interfere with the spectral signals that lie close to the Rayleigh frequency. Both of these problems can require optical components for filtering the exciting and scattered light. In U.S. Pat. No. 5,112,127 by Carrabba and Rauh, these filters are placed at the sampling end of the optical fiber bundle. As placed, the filters are extra components that are subject to chemical and thermal attack by the sample.

U.S. Pat. No. 4,573,761 by McLachlan et al describes apparatus and optical fiber configurations for measuring sensitive Raman analysis in which the collection fibers are cemented at an angle with respect to the excitation fiber to improve signal collection efficiency for remote Raman spectroscopy. This patent also describes the utilization of diamond windows for the determination of species which exhibit Raman spectra in remote corrosive environments.

Diamond windows, although useful in minimizing corrosion, are highly reflective and therefore degrade the intensity of signals coming from outside of the diamond. This patent, however, does not address the problem of removing the spurious or false optical signals originating in the excitation and collection fibers.

Sheng Dai et al describe in *Mikrochimica Acta* (1992), volume 108, the fabrication of a fused all-silica fiberoptic probe having a flat probe tip and its use for obtaining Raman spectra of various molten salt systems at temperatures up to 720° C. The fiberoptic probe has also been used for Raman spectral studies of samples at ambient temperatures.

Current temperature sensors make it difficult, if not impossible, to measure the temperature of high temperature metallic melts. For example, it is currently not possible to continuously measure the temperature of cryolite (NaF—AlF$_3$) melts in the aluminum production industry. Specifically, the only measuring technique currently available for use with cryolite melts involves the use of thermocouples, which are quickly destroyed by the melt. The inability to effectively monitor the temperature of the melt makes it difficult to control the temperature of the melt and improve the efficiency of aluminum production.

Fiber optic thermometers are known for measuring high temperature furnaces. In U.S. Pat. No. 5,201,022 to Shifflett, an optical fiber thermometer system generally includes a black body radiator secured to an optical fiber. The optical fiber has a "hot" end positioned in the furnace being tested and a "cold" end coupled to receiving and decoding electronics. The optical fiber includes a sapphire or silica core with a pure platinum coating.

The Raman spectrum of diamond has been shown to be useful in facilitating temperature measurements. Sheng Dai, J. P. Young, C. M. Begun, Gleb Mamantov, "Temperature Measurement by Observation of the Raman Spectrum, of Diamond," *App. Spectros.*, 46, p. 375 (1992). In this publication, an experimental fiber optic probe included a diamond window placed in a quartz tube. Raman shifts in a transmitted laser light wave were correlated to variations in temperature. The Dai et al. publication is incorporated herein by reference.

Despite the advances disclosed in the prior art, a need does exist for a fiberoptic probe with improved performance for conducting spectral measurements while simultaneously monitoring temperature that is able to withstand the corrosive, hostile environments of a high temperature metallic melt, such as cryolite melts in the aluminum industry, particularly in samples remote from the generating optical energy source and signal analyzer. Therefore, a fiberoptic probe is needed which yields improved performance and requires no epoxy resin or cement to fix the probe tip geometry.

Applicants' probe offers a solution to the need for improved performance and durability. Applicant's probe can be used in a number of high-temperature systems such as molten NaCl—KCl—MgCl$_2$—CaCl$_2$ used in electrolytic production of magnesium metal, various slag containing high temperature systems, etc. Applicant's probe can also find useful application in cryolite type melts (NaF—AlF$_3$—Al$_2$O$_3$) used in electrolytic aluminum production. Applicants' probe is a fiberoptic probe wherein the optical fibers are sealed in fused silica, essentially forming a fused silica rod, with a probe tip that is shaped into unique specific geometrical configurations that are dependent upon the index of refraction of the sample to be analyzed. The probe tip is at least partially protected by a cover, preferably a transparent cover, such as a diamond film. Applicants' probe is fabricated with specific geometrical probe tip configurations for greater optical coupling efficiency of the exciting and collection optical fibers at the sample interface. The unique specific geometrical configurations in which the probe tip can be shaped include a slanted probe tip with an angle greater than 0°, an inverted cone-shaped probe tip, and a lens head. Applicants' probe requires no epoxy resin or cement to fix the probe tip geometry. Since the optical fibers are sealed in fused silica at the probe tip of the fiberoptic probe and the probe tip is protected by a cover, there is no failure of the probe at very low or high temperatures or in hostile environments. The protective cover provides additional protection while acting as a temperature sensor. The angle of the probe tip is generated by grinding and polishing the optical fiber probe tip and can be shaped by standard optical machining practice. Applicants' design is useful for any spectroscopy that uses scattered light, such as Raman, fluorescence, scattered reflection, etc., in a much wider variety of sampling situations. Optical filtering can be carried out away from the sample interface.

OBJECTS OF THE INVENTION

It is an object of the invention to provide new instrumentation for environmental monitoring, characterizing, and locating of hazardous wastes in a timely, cost-effective manner.

It is another object of the invention to provide a new multifunctional fiberoptic probe in which the probe is capable of withstanding the corrosiveness of a high temperature metallic melt.

It is still a further object of the invention to provide a new multifunctional fiberoptic probe for measuring both light scattering and luminescence.

It is another object of the invention to provide a new multifunctional fiberoptic probe particularly for conducting Raman spectral measurements.

It is yet another object of the invention to provide a new multifunctional fiberoptic probe which can be used in a corrosive environment for prolonged periods of time, for continuous monitoring of high temperature melts, such as cryolite.

It is still a further object of the invention to provide a new multifunctional fiberoptic probe which functions for the measurement of concentration of ionic species while simultaneously providing a sensor employing the Raman spectrum produced by a protective material to accurately and reliably obtain temperature information.

It is another object of the invention to provide a new multifunctional fiberoptic probe for the continuous measurement of soluble alumina and soluble aluminum concentration and temperature in molten cryolite.

It is still a further object of the invention to provide continuous or semi-continuous analytical sensors to determine the concentration of soluble magnesium ion in chloride molten salts used in the electrolytic production of magnesium metal.

Further and other objects of the present invention will become apparent from the description contained herein.

SUMMARY

In accordance with one aspect of the present invention, the foregoing and other objects are achieved by a fused fiberoptic probe for conducting electromagnetic spectral measurements which comprises an immersible probe head having a slanted probe tip with an angle greater than 0°, an exciting optical fiber and at least one collection optical fiber. The exciting optical fiber has a terminus at the probe tip for transmitting exciting optical energy to the probe tip in order to generate an optical signal within the sample medium. The collection optical fiber has a terminus at the probe tip. The collection optical fiber is fused with the exciting optical fiber at the probe head, thereby forming the probe head. The terminuses of the exciting optical fiber and the collection optical fiber form the probe tip. The collection optical fiber is for transmitting the optical signal from the probe tip. The fiberoptic probe further has a translucent cover means disposed in the path of the exciting optical energy and disposed over at least a portion of the probe tip.

In accordance with another aspect of the present invention, other objects are achieved by a fused fiberoptic probe for conducting electromagnetic spectral measurements which comprises an exciting optical fiber having a terminus and at least two collection optical fibers, each having a terminus. The fiberoptic probe further comprises an immersible probe head having a longitudinal axis and a perpendicular axis which forms an angle with the terminuses of the exciting optical fiber and the collection optical fibers. The perpendicular axis intersects the longitudinal axis. The probe head further has an inverted cone-shaped probe tip wherein the terminuses of the exciting optical fiber and the collection optical fibers are within the plane of the inverted cone of the conical indentation and thus are angled toward the longitudinal axis at an angle between 10° and 85° with respect to the perpendicular axis, the angle being dependent upon the effective index of refraction of a sample medium. The inverted cone-shaped probe tip has a center apex, the center apex being intersected by the longitudinal axis. The exciting optical fiber's terminus is at the center apex of the inverted cone-shaped probe tip for transmitting exciting optical energy to the probe tip in order to generate an optical signal within the sample medium. The collection optical fibers are juxtaposed with the exciting optical fiber. The collection optical fibers are fused with the exciting optical fiber at the probe head, thereby forming the probe head. The terminus of the exciting optical fiber and the terminuses of the collection optical fibers are within the plane of the conical indentation of the inverted cone-shaped probe tip. The collection optical fibers are for transmitting the optical signal from the probe tip. The fiberoptic probe further comprises a translucent cover means disposed in the path of the exciting optical energy and disposed over at least a portion of the probe tip.

In accordance with yet another aspect of the present invention, other objects are achieved by a fused fiberoptic probe for conducting electromagnetic spectral measurements which comprises a housing, an immersible probe head, wherein the probe head has a probe tip and a lens disposed on the probe tip. The fiberoptic probe further comprises an exciting optical fiber and at least one collection optical fiber. The exciting optical fiber is disposed within the housing and the exciting optical fiber has a terminus at the probe tip for transmitting exciting optical energy to the probe tip in order to generate an optical signal within a sample medium. The collection optical fiber is disposed within the housing and the collection optical fiber has a terminus at the probe tip. The collection optical fiber is fused with the housing and with the exciting optical fiber at the probe head, thereby forming the probe head. The terminus of the exciting optical fiber and the terminus of the collection optical fiber form the probe tip. The collection optical fiber is for transmitting the optical signal from the probe tip. The fused fiberoptic probe further comprises a translucent cover means disposed in the path of the exciting optical energy and disposed over at least a portion of the lens.

In accordance with another aspect of the present invention, a fiberoptic probe system for conducting electromagnetic spectral measurements comprising a fused fiberoptic probe having an immersible probe head having a slanted tip with an angle greater than 0°, an exciting optical fiber having a terminus at the probe tip, at least one collection optical fiber having a terminus at the probe tip, the collection optical fiber being fused with the exciting optical fiber at the probe head thereby forming the probe head, the terminus of the exciting optical fiber and the terminus of the collection optical fiber forming the probe tip, and a translucent cover means disposed in the path of the exciting optical energy and disposed over at least a portion of the probe tip. The fiberoptic probe system further comprising an optical energy source and a signal analyzer. The optical energy source being in optical communication with the exciting optical fiber, wherein the optical energy is coupled into the exciting optical fiber and the optical energy is directed into the sample medium via the probe tip. The optical signal is collected by the collection optical fiber through the probe tip, being directed into the collection optical fiber, and the collection optical fiber being in optical communication with the signal analyzer.

In accordance with still another aspect of the present invention, a fiberoptic probe system for conducting electromagnetic spectral measurements comprising a fused fiberoptic probe having an exciting optical fiber having a terminus and at least two collection optical fibers each having a terminus, an immersible probe head having a longitudinal axis and a perpendicular axis which forms an angle with the terminuses of the exciting optical fiber and the collection optical fibers wherein the perpendicular axis intersects the longitudinal axis, and the probe head further having an inverted cone-shaped probe tip wherein the terminuses of the exciting optical fiber and the collection optical fibers are angled toward the longitudinal axis at an angle between 10° and 85° with respect to the perpendicular axis, the angle dependent upon the effective refractive index of a sample medium, and the inverted coneshaped probe tip having a center apex, the center apex being intersected by the longitudinal axis, and the exciting optical fiber having the terminus at the center apex of the inverted cone-shaped probe tip, the collection optical fibers being juxtaposed with the exciting optical fiber, the collection optical fibers being fused with the exciting optical fiber at the probe head thereby being within the plane of the conical indentation of the probe head and the terminus of the exciting optical fiber and the terminuses of the collection optical fibers forming the inverted cone-shaped probe tip, the fiberoptic probe system further comprising a translucent cover means disposed in the path of the exciting optical energy and disposed over at least a portion of the probe tip. The fiberoptic probe system further comprises an optical energy source and a signal analyzer. The optical energy source is in optical communication with the exciting optical fiber, wherein the optical energy is coupled into the exciting optical fiber, and then the optical energy is directed into the sample medium via the probe tip. The optical signal is collected by the collection optical fibers through the probe tip and is directed into the collection optical fibers, the collection optical fibers being in optical communication with the signal analyzer.

In accordance with yet another aspect of the present invention, a fiberoptic probe system for conducting electromagnetic spectal measurements comprises a fiberoptic probe having a housing, an immersible probe head having a probe tip and a lens disposed on the probe tip, an exciting optical fiber disposed within the housing and the exciting optical fiber having a terminus at the probe tip, at least one collection optical fiber disposed within the housing and the collection optical fiber having a terminus at the probe tip, the collection optical fiber being fused with the housing and with the exciting optical fiber at the probe head thereby forming the probe head, and the terminus of the exciting optical fiber and the terminus of the collection optical fiber forming the probe tip, and a transparent cover means disposed in the path of the exciting optical energy and disposed over at least a portion of the lens. The fiberoptic probe system further comprises an optical energy source and a signal analyzer. The optical energy source is in optical communication with the exciting optical fiber, wherein the optical energy is coupled into the exciting optical fiber and then the optical energy is directed into the sample medium via the lens and the probe tip. The optical signal is collected through the lens and the probe tip by the collection optical fiber, being directed into the collection optical fiber, the collection optical fiber is in optical communication with the signal analyzer.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

The subject invention is a novel yet practical approach for conducting electromagnetic spectral measurements, both light scattering and luminescence, in samples remote from the generating optical energy source and signal analyzer. Applicant's fiberoptic probe is a multi-functional probe generally comprising a probe head having a probe tip, an exciting optical fiber and at least one collection optical fiber fused at the probe head within a housing, preferably an all-silica housing, with a protective cover disposed over at least a portion of the probe tip, essentially forming a fused silica rod. The probe head has a probe tip shaped into unique specific geometrical configurations that are dependent upon the effective index of refraction of the sample to be analyzed. Applicant's probe is fabricated with specific geometrical probe tip configurations for greater optical coupling efficiency of the exciting and collection optical fibers at the sample interface. The unique specific geometrical configurations in which the probe tip can be shaped include a slanted probe tip with an angle greater than 0° a probe tip having a conical indentation at its tip, co-axial with the optical fibers, herein referred to as, an inverted cone-shaped probe tip, and a probe tip with a lens disposed on the probe tip. The optical fibers are silica as well. A protective cover means is applied over the portion of the fiberoptic probe that is to be exposed to the high-temperature corrosive environment to protect the optical fibers from the corrosivity. The protective cover means is a translucent, preferably transparent, chemically inert material having a corrosion resistance quality and also an optical quality. The optical quality is required for temperature analysis.

The design of Applicant's fiberoptic probe allows for long-term chemical stability in a number of high-temperature systems including metallic melts, slag, cryolite melts and molten salts such as molten NaCl—KCl—MgCl$_2$—CaCl$_2$ used in electrolytic production of madnesium metal. The diamond coated probe has application in cryolite type melts (NaF—AlF$_3$—Al$_2$O$_3$) used in electrolytic aluminum production.

Figure 1:
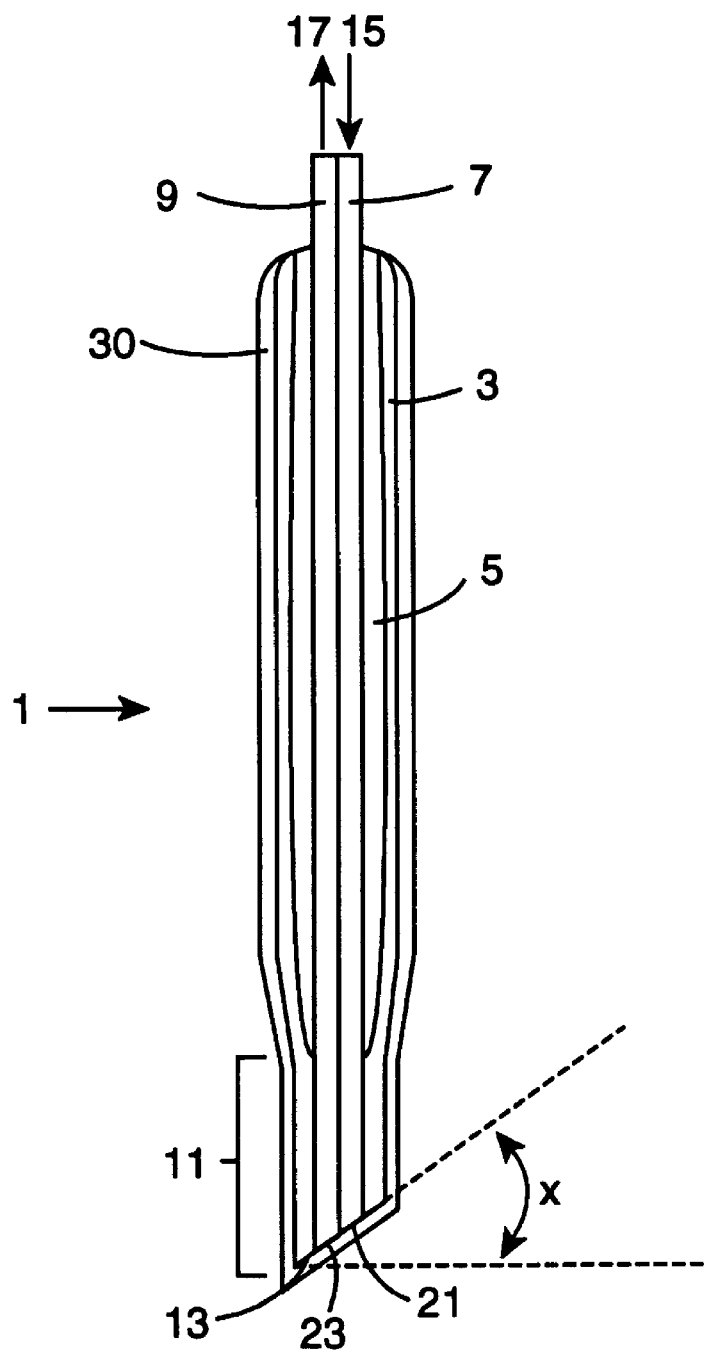
FIG. 1 shows a sectional view of a fused fiberoptic probe with the probe head having a slanted probe tip and a cover means disposed over the probe tip in accordance with one embodiment of the invention.

FIG. 1 shows one embodiment of applicants' invention, a slanted-tip fiberoptic probe 1. This design of the fiberoptic probe aids in collecting electromagnetic emissions such as scattered light (i.e. Raman signals) and luminescence 17, generated by optical energy, such as laser light 15, from an optical energy source. Experimentally, it was found that the slanted-tip probe minimizes the collection of the quartz Raman signals generated in the exciting optical fiber 7. Referring to FIG. 1, the fiberoptic probe 1 comprises two parallel optical fibers 7, 9, an exciting optical fiber 7 and a collection optical fiber 9, that are fused within an all-silica housing 3 at the probe head 11. The optical fibers terminate at their respective terminuses 21, 23 in a probe tip 13 having a slanted tip with an angle x greater than 0°. The probe tip 13 and probe head 11 is immersible in a sample. The probe head 11 is the region of the fiberoptic probe where the housing 3 and the optical fibers 7 and 9 are fused together, actually forming or defining the probe head and then their terminuses are shaped into the slanted tip 13. The fiberoptic probe 1 further comprises a protective cover means 30 that is disposed over the portion of the probe tip and sides that are to be exposed to the corrosive environment that is to be analyzed. As mentioned above, it is important that the cover means be of a translucent material, preferably transparent. Because the fusion of the optical fibers 7, 9 with the housing 3, only at the probe head 11, air pockets 5 are created between the housing 3 and the optical fibers 7, 9. The exciting optical fiber 7 transmits optical energy 15 from any suitable optical energy source (FIG. 9), such as a laser (18 of FIG. 9), to its terminus 21 at the slanted probe tip 13. The optical energy source providing the optical energy is in optical communication with the fiberoptic probe by directing its energy onto the exciting optical fiber 7. The optical energy 15 is transmitted from the slanted probe tip 13 at the terminus of the exciting optical fiber 21 into a sample medium, generating an optical signal 17 from the sample. This is the reason for the protective cover means is made of a translucent material, to allow the optical energy to efficiently be transmitted from the probe tip into the sample medium to generate the optical signal and to allow the optical signal to be efficiently and effectively be collected. The optical signal 17 is collected by the collection optical fiber 9 at the slanted probe tip 13 by the terminus 23 of the collection optical fiber and is transmitted from the slanted tip 13, up the collection optical fiber 9 to a signal analyzer (19 of FIG. 9), such as a spectrometer. The signal analyzer (19 of FIG. 9) is in optical communication with the fiberoptic probe. The signal analyzer (19 of FIG. 9) receives the information from the optical signal 17 via the collection optical fiber 9, analyzes and processes that information.

Figure 2:
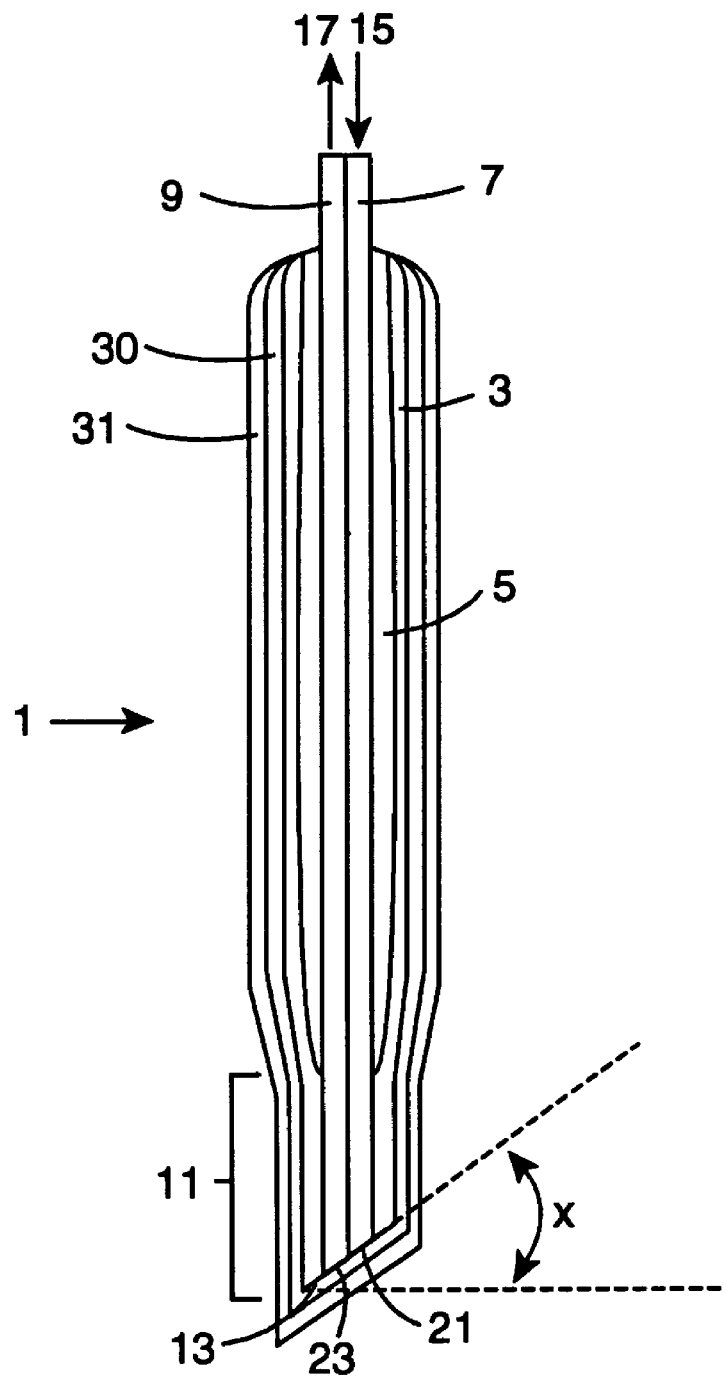
FIG. 2 shows a sectional view of another embodiment of the fused fiberoptic probe with the probe head having a slanted probe tip and the cover means comprising a first and second protective cover disposed over the probe tip.
Figure 3:
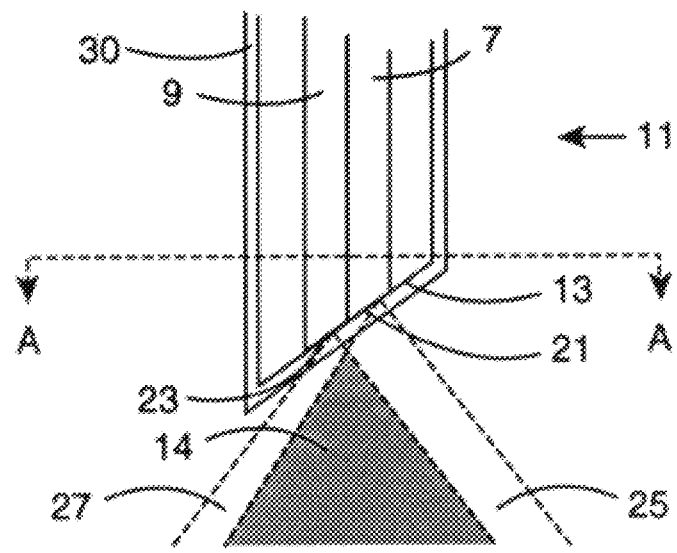
FIG. 3 shows the probe head with the slanted probe tip and the cover means shown in FIG. 1, illustrating the overlap of the geometry of the viewing cones of the exciting optical fiber and the collection optical fiber.
Figure 4:
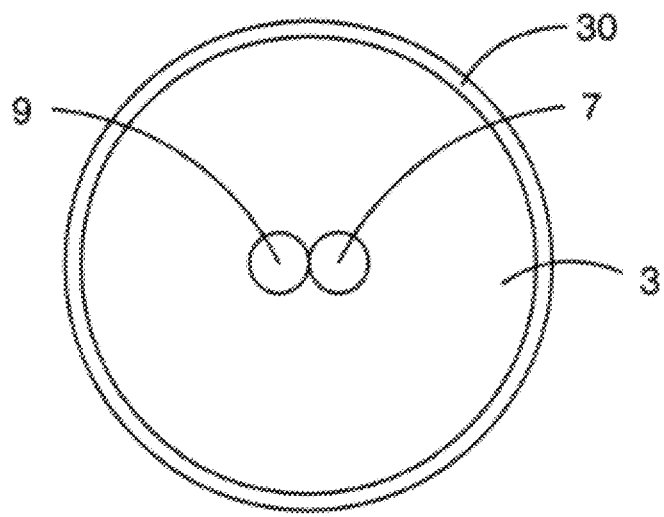
FIG. 4 shows the cross-section from FIG. 3, illustrating the closeness of the exciting optical fiber and collection optical fiber to one another.

This particular embodiment 1 of applicants' fiberoptic probe can be easily created by cutting and polishing a slanted tip, as shown in FIG. 1, out of the uncut, fused probe tip. FIG. 2 is another embodiment of FIG. 1 wherein FIG. 2 shows a second protective cover 31 disposed over the first protective cover 30 of FIG. 1. This second protective cover 31 provides protection against corrosivity and high temperatures for the diamond coating of the first protective cover 30. FIG. 3 illustrates the overlap of the geometry 14 of the viewing cones 27 and 25 of the collection and exciting optical fibers which contributes to the improved collection efficiency of the fiberoptic probe. The improved collection efficiency of the probe is also attributed to the closeness of the optical fibers to one another as a result of the fused design of the probe. FIG. 3 also shows a cross-section cut A that is illustrated in FIG. 4. FIG. 4 illustrates this close relationship of the exciting optical fiber 7 with the collection optical fiber 9, both optical fibers being fused within the housing 3 at the probe head with 30 being the protective cover. The closer the optical fibers are to one another, the larger the area of the overlap 14 of FIG. 3. By increasing the area of the overlap 14, the collectible Raman scattering is intensified, thereby increasing the optical signal. This closeness is achievable because the optical fibers 7 and 9 are positioned together by the fusion step in the fabrication of the probe head 11. The arrangement of the present invention in FIG. 1 and FIG. 2 minimizes the background quartz signals. The collection optical fiber 9 does not pick up the scattered Raman signal from the exciting otpical fiber 7, so the quartz interference is minimized. There is no "crosstalk" or communication between the exciting and collection optical fibers.

The optimum angle for the slant is related to the effective index of refraction of the sample medium. Essentially the effective refractive index controls the diameter of the viewing cones 27 and 25 of FIG. 3 of the exciting and collection optical fibers, and therefore influences the overlap 14. Any angle greater than 0°, particularly between 10° and 85°, is going to show improvement in scattered light collection over that of a flat-tip fiberoptic probe. It is probable that an angle of about 50° will be optimum for most applications.

Figure 5:
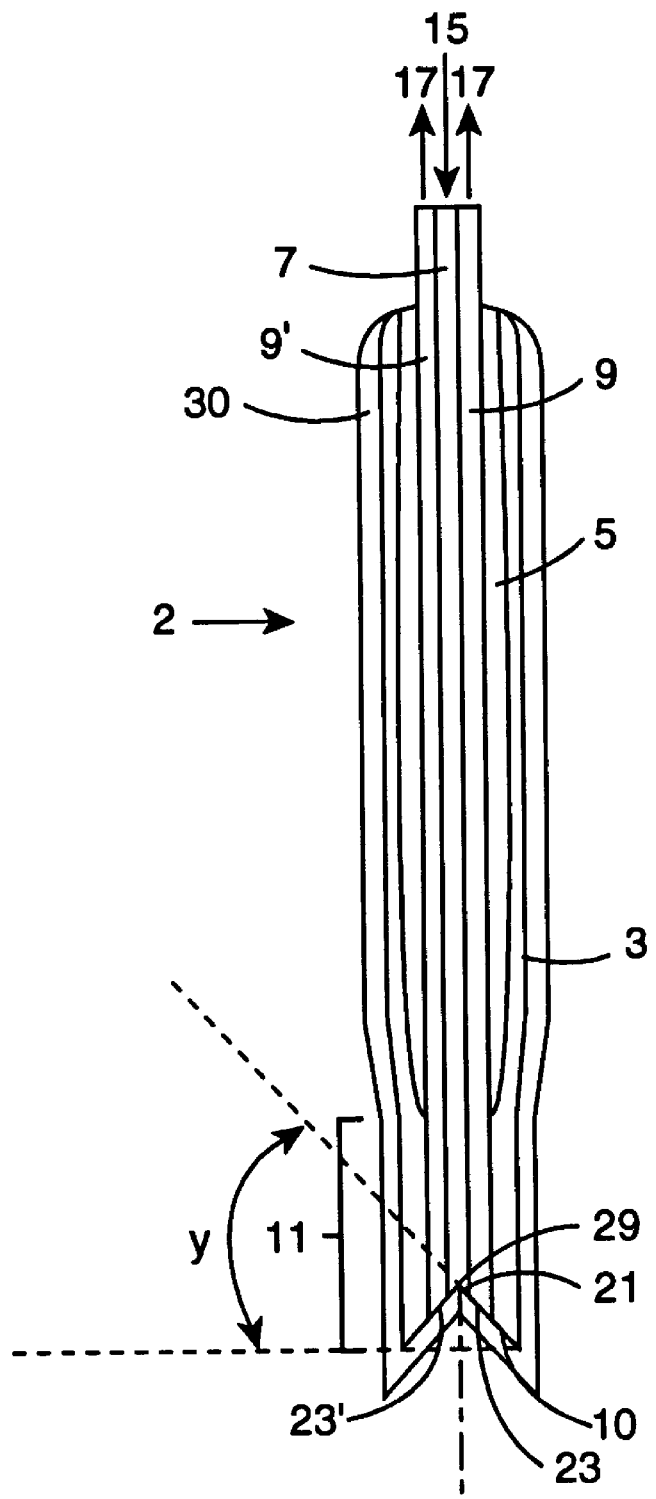
FIG. 5 illustrates, in accordance with another embodiment of the invention, a sectional view of a fused fiberoptic probe with the probe head having an inverted cone-shaped probe tip with the exciting optical fiber positioned at the center apex of the cone and at least two collection optical fibers juxtaposed with the exciting optical fiber and a cover means disposed over the probe tip.
Figure 6:
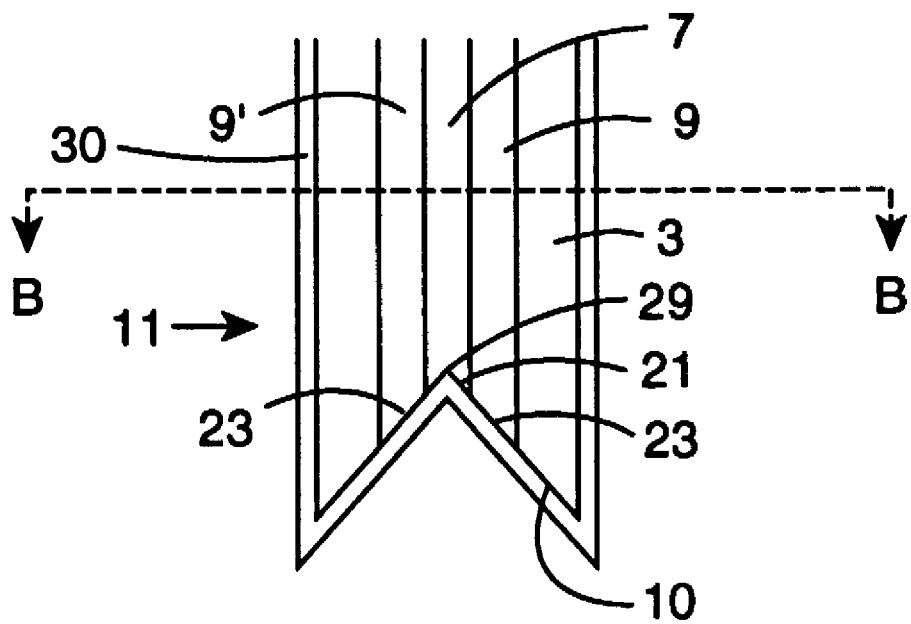
FIG. 6 shows the probe tip region of the inverted cone-shaped fiberoptic probe having the cover means disposed over the probe tip.
Figure 7:
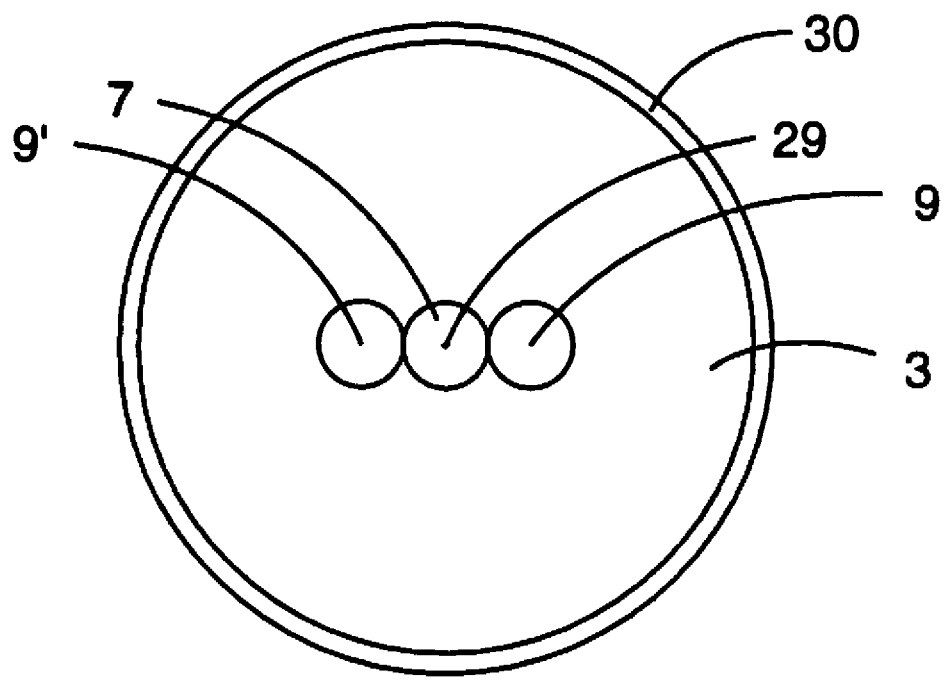
FIG. 7 shows a cross-sectional view of FIG. 6, illustrating the positions and closeness of the exciting optical fiber and the collection optical fibers to one another within the housing of the fiberoptic probe.

FIG. 5 shows another embodiment of a fiberoptic probe 2 wherein the probe tip 10 has the geometrical configuration of a conical indentation at its tip, co-axial with the optical fibers, herein referred to as an inverted cone, wherein the optical coupling of each collection optical fiber is optimized. This embodiment 2 of the fiberoptic probe comprises a probe head 11 having a probe tip with the shape of an inverted cone 10, an exciting optical fiber 7 and at least two collection optical fibers 9, 9'. The fiberoptic probe 2 further comprises a protective cover 30 disposed over the portion of the probe to be exposed to the corrosive environment that is to be analyzed. The exciting optical fiber 7 is for transmitting exciting optical energy 15 from an energy source to the probe tip 10 in order to generate an optical signal 17 within a sample medium. The collection optical fibers 9, 9' are for transmitting the optical signal 17 from the probe tip. The figure shows the exciting optical fiber 7 having a terminus 21 at the center apex 29 of the cone, with the collection optical fibers 9 and 9' juxtaposed with the exciting optical fiber 7, surrounding the exciting optical fiber. The collection optical fibers have terminuses 23 and 23' juxtaposed with the exciting optical fiber terminus 21, therefore surrounding the center apex 29. The fusion of the housing 3 and the exciting and collection optical fibers is the probe head 11, thereby forming or defining the probe head, as with the slanted tip fiberoptic probe of FIG. 1. The fusion step creates the air pockets 5. The geometry of the inverted cone-shaped probe tip 10 is actually a multiple slanted-tip fiberoptic probe, a three-dimensional slanted-tip fiberoptic probe. The multiplicity is equal to the number of collection optical fibers 9, 9' that are juxtaposed with the exciting optical fiber 7 at the apex of the cone 29. Since each collection optical fiber 9, 9' is immediately adjacent and tangentially touching the exciting optical fiber, maximum collection efficiency of the collection optical fibers is realized. Again, this unique feature is possible because of the construction of the fused fiberoptic probe 2. FIG. 5 shows the probe head 11 having a longitudinal axis intersecting the apex of the inverted cone. A perpendicular axis is also shown intersecting the longitudinal axis at the probe head and probe tip. The terminuses of the exciting optical fiber 21 and the collection optical fibers 23, 23' are within the plane of the inverted cone of the conical indentation and thus are angled toward the longitudinal axis at an angle between 10° and 85° with respect to the perpendicular axis. The angle y, representing the angle of the terminuses of the optical fibers at the probe tip 10, depends upon the effective refractive index of the sample with an optimum angle between 10° and 85°. FIG. 6 shows a sectional view of the probe head 11 with a cross-cut B with the exciting optical fiber 7 having its terminus 21 at the center apex 29 of the inverted cone probe tip 10, collection optical fibers 9 and 9' being juxtaposed with the exciting optical fiber 7 with their terminuses 23 and 23' at the probe tip 10, fused within housing 3 and the protective cover 30 disposed over a portion of the fiberoptic probe. FIG. 7 shows the cross-cut view from FIG. 6, illustrating the closeness and positions of the collection optical fibers 9 and 9' surrounding and juxtaposed with the exciting optical fiber 7 within the housing 3. The center apex 29 of the inverted cone can be seen in the center of the exciting optical fiber 7 since the exciting optical fiber 7 is positioned at the center apex 29. The preferred embodiment of the inverted cone-shaped fiberoptic probe 2 has six collection optical fibers surrounding and juxtaposed with the exciting optical fiber. The embodiment shown in FIG. 6 is very useful for reflectance spectroscopy since it results in more efficient collection of scattered light. The cone-shaped probe tip 10 of the fiberoptic probe 2 can also act as a cuvette or a spectroscopy container when the probe is inverted, holding a very small volume of sample, either liquid or solid. For example, if the probe tip comprised one exciting optical fiber and six collection optical fibers of 100 μm in diameter, the seven optical fibers in this inverted conical tip (cone angle approximately 50°) would be covered by only 4 nl of liquid. Such an embodiment would be useful for microspectrophotometry, Raman, fluorescence or absorption. This probe tip would be useful for fluorescence studies of materials adsorbed on single resin beads of about 100 μm in diameter. The collection efficiency is very high with this embodiment. Solid, liquid or powder samples can be analyzed using this probe and method.

Figure 8:
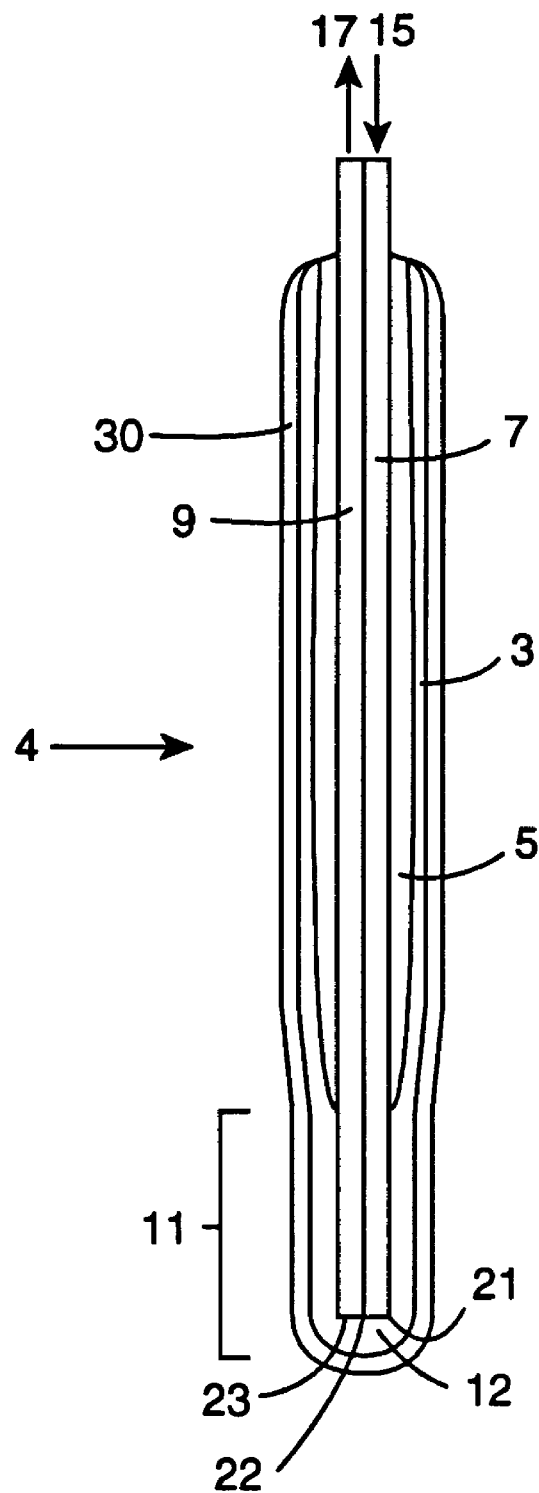
FIG. 8 shows a sectional view of a fused fiberoptic probe with the probe head having a probe tip with a lens disposed on the probe tip and a cover means disposed over the lens and probe tip, in accordance with another embodiment of the invention.

FIG. 8 shows yet another embodiment of the fiberoptic probe 4. This particular embodiment comprises the same probe body style as in FIG. 1, except that the probe head 11 has a convex lens 12 disposed on the probe tip 22 wherein the housing 3 extends beyond the terminuses 21 and 23 of the optical fibers 7 and 9, (which make up the probe tip), to form the lens 12. The lens 12 can also be disposed on the probe tip 22 by using a sol-gel technique. The lens head fiberoptic probe 4 comprises a probe head having a convex lens 12 disposed on the probe tip 22, an exciting optical fiber 7 and at least one collection optical fiber 9 fused within a housing 3 at the probe head, thereby forming the probe head. The exciting optical fiber 7 and the collection optical fiber 9 each have a terminus at the probe tip 22, 21 and 23, respectively, thereby forming the probe tip. The fiberoptic probe further comprises a protective cover 30 disposed over the portion of the fiberoptic probe to be exposed to the corrosive environment that is to be analyzed. The exciting optical fiber is for transmitting exciting optical energy 15 to the probe tip in order to generate an optical signal 17 within the sample medium. The collection optical fiber 9 has a terminus 23 at the probe tip 22 for transmitting the optical signal 17 from the probe tip 22 to a signal analyzer. The probe head 11 is the region of the probe where the fusion of the optical fibers 7, 9 and the housing 3 occur, creating an air pocket 5 between the housing and optical fibers on the upper body of the probe. The housing 3 and the optical fibers 7, 9 are silica.

The lens 12 can be made by two different techniques. One technique involves heating silica at a higher temperature than the temperature required to fuse the optical fibers with the housing, thus sealing the housing. Then the housing is cut beyond the terminuses of the optical fibers and a lens is ground using standard optical fabrication techniques as described by E. B. Shand in the *Glass Engineering Handbook*, chapter 9 (1958). The second technique is for the lens to be made by adding a drop of sol gel to the probe tip 22 or dip-coating the probe tip in the sol-gel solution. A fiberoptic probe with the probe tip 22 covered with a sol-gel lens was fabricated by the applicants. Sodium silicate solution was used as a sol-gel starting material. The probe tip was dip-coated with the solution and dried vertically in the open air. Gravity and surface tension deformed the shape of the sol-gel naturally into a semi-sphere.

The fabrication of the fiberoptic probe 1 of FIG. 1 involves flame fusing at least two 600 μm diameter optical fibers (C-Technology, Short Hills, N.J.) into a housing, preferably an all-silica tube, with the tube being under a partial vacuum (less than 0.5 atmosphere). Optical fibers with various other diameters can also be used, such as 200 μm and 400 μm. The optical fibers can be of varying lengths as well, depending upon the intended application of the fiberoptic probe. The optical fibers are fused with the all-silica housing tube. The optical fibers have an outer coating of polyimide, but the polyimide coating around the fusion region of each fiber is removed by the flame of a torch before the fibers are fused. The region of the fiberoptic probe where fusion takes place, probe head 11, can be seen in FIG. 1, FIG. 2, FIG. 2, FIG. 5 and FIG. 8. The application of the reduced pressure, mentioned above, during fusion is crucial while pulling the tube around the fibers, in order to make a vacuum tight seal at the probe tip and to prevent bubbling during the closure. The fusion process involves heating the region of the fiberoptic probe 11 to be fused to a temperature sufficient to effect -total fusion wherein the optical fibers are fused with the housing. The fusion method to be used is very similar to those methods used in the fabrication of microelectrodes. An example of this fusion method can be found in *Analytical Chemistry* volume 63, (1991), page 78 by C. Lee, C. J. Miller and A. J. Bard. Once fused, the sealed end of the probe tip is cut. When the above fabrication is complete, the probe head having a probe tip is essentially a silica rod in which the probe tip is then shaped into the desired geometrical configuration mentioned above, using standard optical fabrication techniques as described in chapter 9 of the *Glass Engineering Handbook*, McGraw-Hill 1958 by E. B. Shand. Once the probe tip is shaped then a protective cover is applied to at least a portion of the probe tip, disposed over the path of the exciting optical energy. A protective cover means is applied over the portion of the fiberoptic probe that is to be exposed to the high-temperature corrosive environment to protect the optical fibers from the corrosivity. The protective cover means is a translucent, preferably transparent, chemically inert material having a corrosion resistance quality and also an optical quality. The optical quality is required for temperature analysis.

The protective cover means comprises a first protective cover. Preferably, the protective cover is a diamond coating formed on the probe tip disposed over the path of the exciting optical energy by any suitable means. One example of forming the protective cover is chemical vapor deposition (CVD). While diamond is preferred, other translucent materials may be employed, such as zirconium dioxide, titanium nitride and boron nitride. Synthetic diamond materials may also be employed. The material of the first protective cover is a translucent material which exhibits a well-defined Raman signal that yields a single peak for a particular species.

Where the fiberoptic probe is to be used in melts which are more corrosive to carbonbased coatings, such as diamond, the protective cover means further comprises a second protective cover. The second protective cover is also made of a translucent material resistive to high-temperature corrosive environments. The second protective cover is made from translucent materials such as zirconium dioxide, titanium nitride and boron nitride. It is preferable that the second protective cover be transparent.

The slanted-tip embodiment and other embodiments thereof present a significant improvement in design as it is made from fused silica with no cement involved. It is essentially a silica rod having a protective coating that operates over the temperature range in which silica remains solid (absolute 0 to 1800K). Silica has a very low coefficient of thermal expansion. It has good stability to radiation effects as well as the thermal, optical, and corrosion resistance attributes of pure silica. Therefore, the probe can tolerate these temperature extremes and high radiation fields without failure. The ability to obtain varied kinds of electromagnetic spectral information, not just Raman or absorption, over such a wide range of temperatures and conditions is the unique feature of applicants' fiberoptic probe. At 77K, or below, since the probe can be in intimate contact with the sample, no bubbling of liquid nitrogen or helium is present to interfere with data collection. In corrosive molten chloride salts, the collection of Raman spectra is not affected even when the probe and silica sheath are etched. The probe works as a multifunctional fiberoptic probe because it can scatter exciting light and can collect nearby scattered light.

Figure 9:
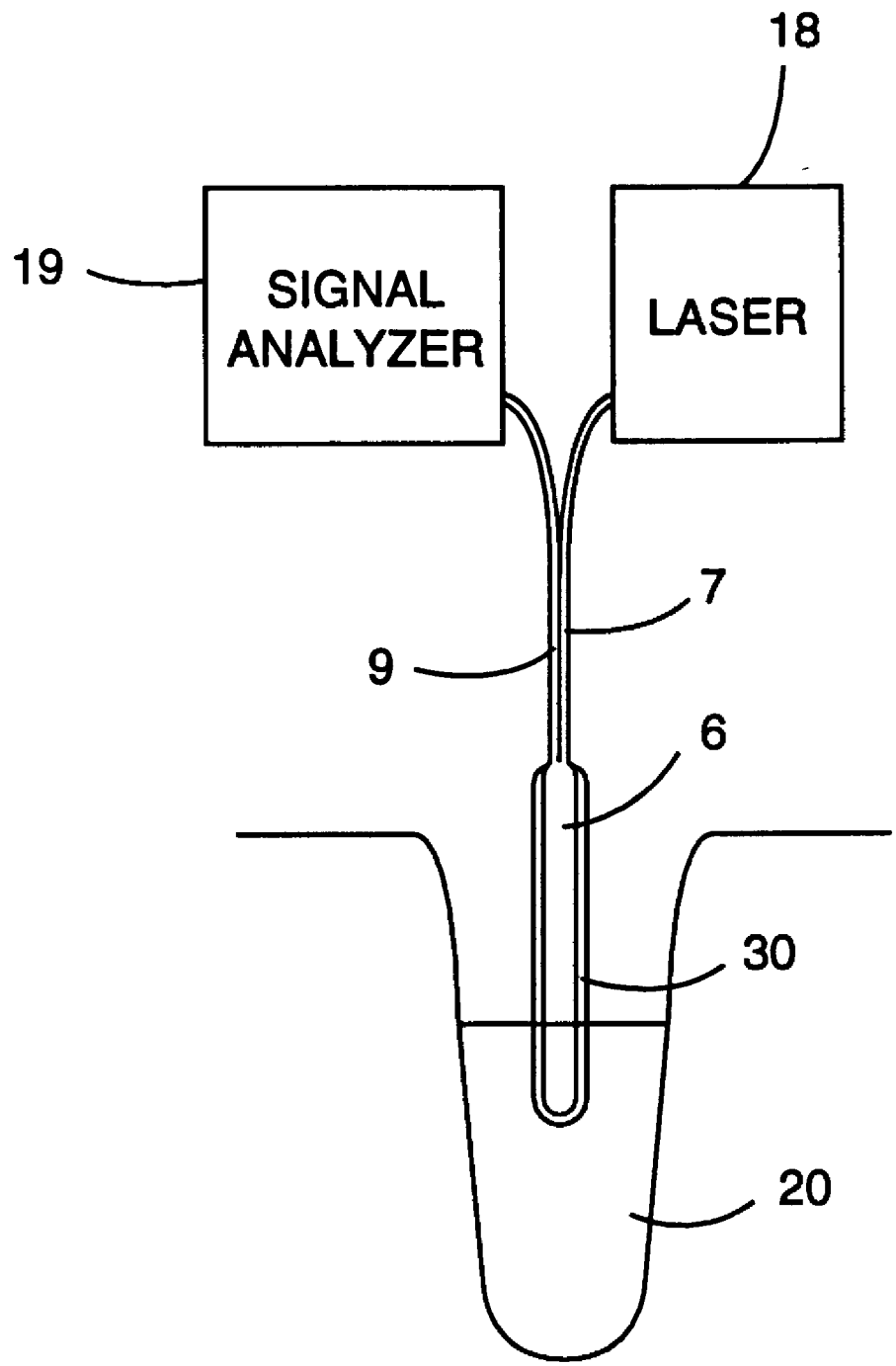
FIG. 9 shows a fiberoptic probe system for conducting electromagnetic spectral measurements utilizing a fused fiberoptic probe having a cover means, in accordance with the invention.

FIG. 9 shows a fiberoptic probe system for conducting spectral measurements utilizing a fiberoptic probe 6 wherein the exciting optical fiber 7 extends beyond the fiberoptic probe body to an optical energy source 18, such as an argon-ion laser. The collection optical fiber 9 extends beyond the fiberoptic probe body to a signal analyzer 19, such as a Ramanor HG.2S spectrophotometer by Jobin-Yvon Instruments SA This particular instrument uses a double monochromator equipped with curved holographic gratings. A S-20 type cooled photomultiplier tube can be used with pulse counting electronics and a Nicolet 1170 signal averager to collect data. The system further comprises a protective cover means 30 disposed over the fiberoptic probe to prevent the melt or sample 20 from corroding that portion of the optical fibers and the probe body which is disposed in the sample. The system in use directs the optical energy from the optical energy source 18 onto the exciting optical fiber 7. The exciting optical fiber 7 then transmits the optical energy to the probe tip and then from the probe tip into the sample medium 20 to generate an optical signal within the sample. At least one collection optical fiber 9 collects the optical signal through the probe tip and transmits the optical signal up the collection optical fiber to the signal analyzer 19. Spectra can then be processed with a personal computer and commercially available data acquisition software. All of these are described in the Dai et al publication. FIG. 9 shows the fiberoptic probe 6 immersed in a sample 20.

Applicant's fiberoptic probe and system have multiple functions that are carried out simultaneously due to its design of the probe head, the materials used in construction and the application of the translucent protective cover means. A material that is transparent is preferred. The preferred transparent material used for the cover means is diamond. Diamond exhibits a well-defined Raman spectrum that can be used for high temperature measurement and for simultaneous measurement of concentration of different species within the melt or sample. It is expected that the probe would last for months to years of service, depending on the thickness of the diamond coating.

The Raman signal is excited by transmitting optical energy down the exciting fiber to the probe tip. Preferably, the exciting energy is in the visible or ultraviolet range, however, radiation having other wavelengths could be used. The exciting energy interacts with the diamond coating at the probe tip to produce a Raman scattered light. This scattered light then passes from the probe tip up the collection optical fiber to the signal analyzer where it is measured and analyzed to determine the temperature of the diamond protective cover and the environment of the sample medium while providing data for the determination of concentration of a species that is present in the sample. The ratio of the Stokes to anti-Stokes Raman line of diamond can be correlated to temperature over the range of about 350° to greater than 2,100° C. (i.e., the thermal stability limit of diamond). The temperature determination using the Stokes/anti-Stokes Raman line is explained in "Temperature Measurement by Observation of the Raman Spectrum, of Diamond," *Applied Spectroscopy*, 46 (1992), p. 375, by Sheng Dai, J. P. Young, G. M. Begun and Gleb Mamantov. As long as the diamond protective cover remains in tact, the temperature of the melt is measurable by the Raman signals being transmitted through the optical fibers. The wavelengths present in the scattered radiation or scattered light collected are characteristic of the structure of the molecule, and the intensity of the radiation is dependent on the concentration of the molecules. The spectrum produced by the scattered radiation or scattered light also varies depending upon the temperature of the molecule.

Although the fiberoptic probe has particular applicability to the aluminum production industry, the probe may be used measuring the temperature and concentration of species in a variety of melts.

While there has been shown and described what are at present considered the preferred embodiments of the invention, it will be obvious to those skilled in the art that various changes and modifications can be made therein, without departing from the scope of the invention defined by the appended claims.

What is claimed is:

1. A fused fiberoptic probe for conducting spectral measurements comprising:
   a. an exciting optical fiber having a terminus;
   b. at least two collection optical fibers, each having a terminus;
   c. an immersible probe head enclosing the terminuses of and being fused to said exciting optical fiber and said collection optical fibers, said immersible probe head having a longitudinal axis and a perpendicular axis, said probe head further having a probe-tip having a conical indentation at its tip, said conical indentation being co-axial with said longitudinal axis, said conical indentation defining a conical surface of an inverted cone-shaped probe tip wherein said terminuses of said exciting optical fiber and said collection optical fibers are within the conical surface of the inverted cone of the conical indentation and thus are angled toward said longitudinal axis at an angle between 10° and 85° with respect to said perpendicular axis, said angle being dependent upon the effective refractive index of a sample medium, said inverted cone-shaped probe tip having a center apex, said center apex being intersected by said longitudinal axis;
   d. said exciting optical fiber having said terminus at said center apex of said inverted cone-shaped probe tip, said exciting optical fiber for transmitting exciting optical energy to said probe tip in order to generate an optical signal within said sample medium;
   e. said collection optical fibers being juxtaposed with said exciting optical fiber, said collection optical fibers for transmitting said optical signal from said probe tip; and
   f. a translucent cover means disposed in the path of said exciting optical energy and disposed over at least a portion of said probe tip.

2. The fiberoptic probe in accordance with claim 1 wherein said exciting and collection optical fibers are fused within a housing of silica.

3. The fiberoptic probe in accordance with claim 1 wherein said translucent cover means comprises a first protective cover made of a translucent material which exhibits a well-defined Raman signal.

4. The fiberoptic probe in accordance with claim 3 wherein said first protective cover is made of a translucent material selected from the group consisting of zirconium dioxide, titanium nitride, boron nitride and diamond.

5. The fiberoptic probe in accordance with claim 1 wherein said translucent cover means is transparent.

6. The fiberoptic probe in accordance with claim 1 wherein said translucent cover means comprises a diamond film coating deposited on said probe tip by chemical vapor deposition.

7. The fiberoptic probe in accordance with claim 3 wherein said translucent cover means further comprises a second protective cover being made of a translucent material resistive to metallic melts and disposed over said first protective cover.

8. The fiberoptic probe in accordance with claim 7 wherein said second protective cover is made of a translucent material selected from the group consisting of zirconium dioxide, titanium nitride, and boron nitride.

9. The fused fiberoptic in accordance with claim 7 wherein said translucent material is transparent.

10. A fiberoptic probe system for conducting electromagnetic spectral measurements comprising the fused fiberoptic probe in claim 1, said system further comprising an optical energy source and a signal analyzer, said optical energy source being in optical communication with said exciting optical fiber, wherein said optical energy is coupled into said exciting optical fiber, said optical energy is directed into said sample medium via said probe tip, and said optical signal is collected by said collection optical fibers through said probe tip, being directed into said collection optical fibers, and said collection optical fibers being in optical communication with said signal analyzer.

11. The fiberoptic probe system in accordance with claim 10 wherein said optical energy source is a laser source transmitting a beam of laser light of a specific wavelength.

12. The fiberoptic probe system in accordance with claim 10 wherein said exciting and collection optical fibers are fused within a housing of silica.

13. The fiberoptic probe system in accordance with claim 10 wherein said signal analyzer is a spectrometer comprising a monochromator and a detector.

14. The fiberoptic probe system in accordance with claim 10 wherein said translucent cover means comprises a first protective cover made of a translucent material which exhibits a well-defined Raman signal.

15. The fiberoptic probe system in accordance with claim 14 wherein said first protective cover is made of a translucent material selected from the group consisting of zirconium dioxide, titanium nitride, boron nitride and diamond.

16. The fiberoptic probe system in accordance with claim 10 wherein said translucent cover means is transparent.

17. The fiberoptic probe system in accordance with claim 10 wherein said translucent cover means comprises a diamond film coating deposited on said probe tip by chemical vapor deposition.

18. The fiberoptic probe system in accordance with claim 14 wherein said translucent cover means further comprises a second protective cover being made of a translucent material resistive to metallic melts and disposed over said first protective cover.

19. The fiberoptic probe system in accordance with claim 18 wherein said second protective cover is made of a translucent material selected from the group consisting of zirconium dioxide, titanium nitride, and boron nitride.

20. The fiberoptic probe system in accordance with claim 18 wherein said translucent material is transparent.

* * * * *